United States Patent [19]

Linkow

[11] Patent Number: 5,110,293
[45] Date of Patent: * May 5, 1992

[54] NECKLESS BLADE IMPLANT

[76] Inventor: Leonard I. Linkow, 1530 Palisade Ave., Fort Lee, N.J. 07024

[*] Notice: The portion of the term of this patent subsequent to Apr. 7, 2009 has been disclaimed.

[21] Appl. No.: 252,290
[22] Filed: Sep. 30, 1988
[51] Int. Cl.5 ............................. A61C 8/00
[52] U.S. Cl. ................................. 433/176
[58] Field of Search .............. 433/173, 176; 228/115

[56] References Cited

U.S. PATENT DOCUMENTS

| | | | |
|---|---|---|---|
| 3,683,501 | 8/1972 | Edelman | 433/176 |
| 3,837,080 | 9/1974 | Pasqualini | 433/176 |
| 3,992,780 | 11/1976 | Herskovits | 433/176 |
| 4,002,284 | 1/1977 | Suppus | 228/115 |
| 4,024,638 | 5/1977 | Linkow et al. | 433/176 |
| 4,223,412 | 9/1980 | Aoyagi et al. | 433/176 X |
| 4,522,596 | 6/1985 | Ashkinazy | 433/176 X |
| 4,531,917 | 7/1985 | Linkow et al. | 433/176 |
| 4,600,388 | 7/1986 | Linkow | 433/176 |
| 4,661,066 | 4/1987 | Linkow et al. | 433/176 |
| 4,804,132 | 2/1989 | DiFrancesco | 228/115 |
| 4,854,874 | 8/1989 | Neuwirth | 433/176 |
| 4,997,383 | 3/1991 | Weiss et al. | 433/176 |

Primary Examiner—Robert P. Swiatek
Assistant Examiner—Nicholas D. Lucchesi
Attorney, Agent, or Firm—Darby & Darby

[57] ABSTRACT

An oral implant for supporting an artificial tooth structure has an implant portion with a connection part in which a lateral dimension is as wide as the lateral dimension of the rest of the implant portion. The implant portion is adapted to be fitted in an opening in a bone in the vicinity of the occlusal plane of a patient in such a manner that at least a part of the connection part extends beyond a rim of the openings in the bone or can remain just below the bone while the base of the post rests on the bone. There is at least one post portion having first and second ends. The first end is adapted to receive at least a part of the artificial tooth structure. The second end is adapted for a direct connection to the connection part of the implant portion. The post portion has lateral dimensions such that a part of the second end extends from sides of the connection part and defines shoulders for supporting the artificial tooth structure.

29 Claims, 2 Drawing Sheets

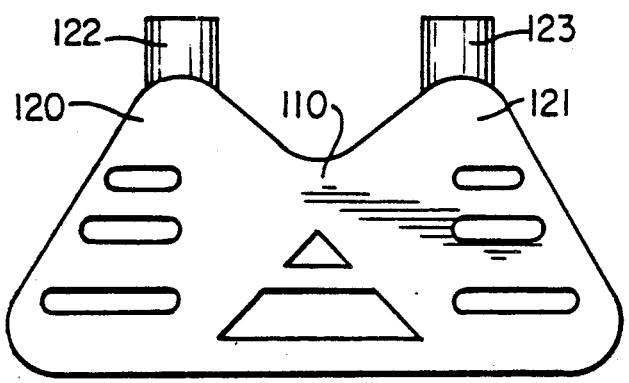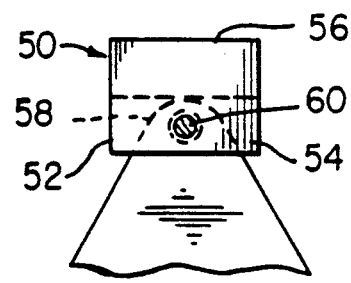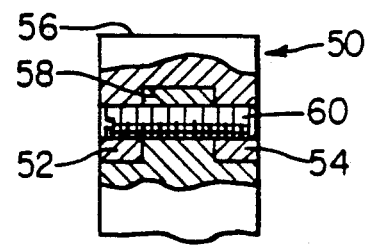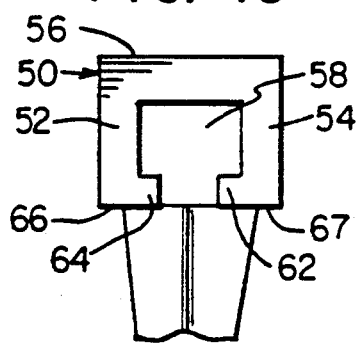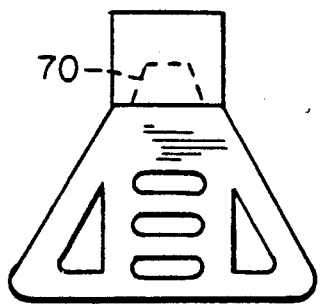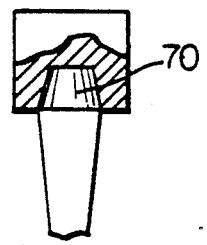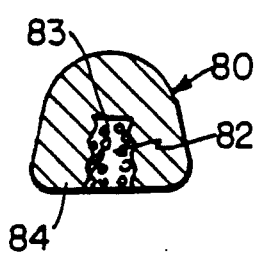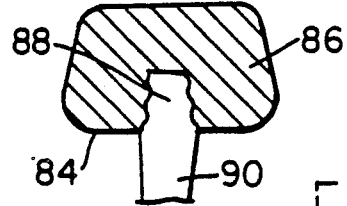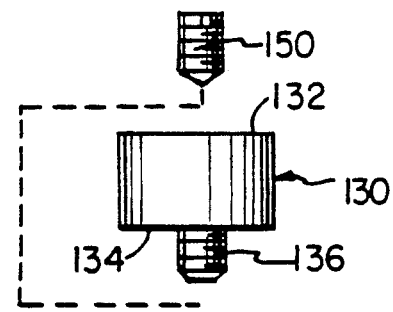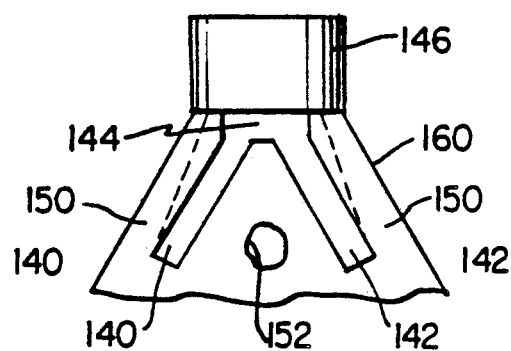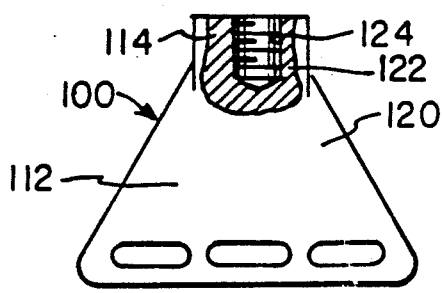

NECKLESS BLADE IMPLANT

BACKGROUND OF THE INVENTION

This invention relates to dental implants and, more particularly, it relates to neckless blade implants.

A dental implant, such as that described in U.S. Pat. Nos. 3,465,441 and 3,660,899 of the present inventor are used to support an artificial bridge, tooth or other dental prosthesis. The implant has an implant portion, e.g. in the form of a blade, that is secured in the underlying bone in an edentulous span. A post portion, typically with a recessed neck part, extends up form the implant portion and supports the artificial bridge or crown. This type implant is inserted by making an incision in the fibromucosal tissue down to the underlying alveolar ridge crest bone. The tissue is then reflected to expose the bone and a burr is used to create a groove in the bone which is as deep as the implant portion. The implant portion is then wedged into the bone. After the insertion, the tissue is sutured about the neck part so that the rest of the post protrudes above the tissue line. Typically, a few weeks or months are allowed to pass before the dental prosthesis is attached to the post. During this period, bone starts to grow around the implant portion and through holes provided in it, thereby acting to anchor the implant in place before it is stressed by use.

Submergible blade implants, such as that shown in U.S. Pat. No. 4,177,562 of A. L. Miller and A. J. Viscido, allow a blade to be inserted in the jawbone for a long period of time before being placed in actual use. With this type of implant the blade is completely submerged in the bone. It is then covered over and allowed to remain in place for several months. For this period it is protected against being dislodged by the tongue or other teeth during mastication. Once there has been substantial regrowth of the bone over, around and through the submerged blade, the tissue is again opened and the post is attached to the blade by a typical screw connection.

As noted, it is common for many types of oral implants disclosed by the prior art to have a post with a neck portion which connects to a blade. Such a neck portion is typically much narrower than the rest of the post and the blade. In view of that, a step-type transitioned area is defined between the post and the blade. Steep variation between the dimensions of the blade, post and the neck makes the transitioned area subject to a much greater concentration of the stresses than other areas of the implant. All this makes the design of the narrow neck the weak spot of the oral implants disclosed by the prior art. In use, such implants can bend in the area of the neck portion when chewing movements are performed. This might cause bone resorption immediately below the neck portion and cause the neck to break.

U.S. Pat. No. 4,178,686 to Riess et al. provides an oral implant in which the implant portion is a polymer matrix having spherical particles of tricalciumphosphate ceramic embedded in its exterior. A post portion has an elongated core member extending substantially into the implant portion. The base of the top part of the post portion extends to the outer edges of the implant portion and tapers inward in the part towards the artificial tooth support. The tooth support itself may be attached to the post by means of a threaded shaft. With this arrangement, the forces of mastication are resisted solely by the threaded shaft, which is relatively narrow, and/or the narrow core portion of the post.

The present inventor's own U.S. Pat. No. 4,600,388 discloses a blade in which the post is designed to straddle recessed portions in the blade. Because of these recessed portions in the blade, the post does not extend beyond the outer limits of the blade. Further, the legs of the post, that allow it to straddle the blade, are relatively thin and these thin legs must resist the forces of masticatiom. Further, there is no direct means for rigidly securing the post to the blade, other than the nature spring force of the legs of the post.

The relatively narrow neck portions of posts in prior art implants are subject to bending and breakage during normal use. When this occurs it is often necessary to remove part or all of the implant, including the blade portion, to repair the damage. Thus, it would be extremely advantageous if blade implants could be provided with extremely rugged post portions which could easily resist the forces of mastication.

SUMMARY OF THE INVENTION

The present invention provides an oral blade-type implant for supporting an artificial tooth structure in which (a) the traditional recessed neck portion of the support post is eliminated, and (b) one end of the post is adapted for a direct connection to the blade and has a width and length such that the post base extends outwardly from sides of the blade, thus defining shoulders for support of the artificial dental structure.

In an illustrative embodiment of the invention, the oral implant for supporting an artificial tooth structure includes an implant portion in the form of a blade. This blade is adapted to be fitted in an opening in the patient's mandible or maxilla in the vicinity of the occlusal plane. On the edge of the blade directed toward the occlusal plane, the blade has at least one connection part that projects toward the occlusal plane. The installation of the blade in the bone is such that at least a portion of the connection part extends out of the bone. At least one post portion is adapted to receive at least a part of the artificial tooth structure at the end and is directly connected to the connection part of the implant portion at its base or other end. The post has a size at its base such that it extends outwardly from sides of the connection part, defining shoulders for supporting the artificial tooth structure.

In a preferred embodiment the implant portion has a substantially triangular configuration. The connection portion of the implant part is positioned at one angle of the triangle and the shoulders of the base of the post extend outwardly from the sides of the triangle. The shoulders of the base of the post overlap surfaces of the connection part of the implant portion in the bucco-lingual direction. Also the shoulders may extend from the connection part of the implant portion in the bucco-lingual direction. A cross-section of the implant portion in the bucco-lingual direction can have a wedge-shaped configuration with wide and narrow sides. The wide side in this arrangement is connected to the base of the post portion.

In another embodiment the implant portion has a bending arrangement to enable the oral implant to be bent in the mesiodistal direction. The bending arrangement is achieved with a pair of V-shaped slits, one on each side of the connection part.

In a still further embodiment the post portion is detachably connected to the implant portion and the second or base end of the post portion is adapted to straddle the connection part of the implant portion. The base of the post portion has a pair of spaced apart legs and the connection part of the implant portion has a pair of recesses. In the assembled condition of the oral implant the legs fit within the recesses of the implant portion.

BRIEF DESCRIPTION OF THE DRAWINGS

Other advantages and features of the invention are described with reference to exemplary embodiments, which are intended to explain and not to limit the invention, and are illustrated in the drawings in which:

FIG. 10 is a view of the dental implant with two posts.

FIG. 11 is a partial view of a still further embodiment of the dental implant.

FIG. 12 is a side cross-sectional view of FIG. 11.

FIG. 13 is an enlarged broken view of the dental implant.

FIG. 14 is a view of a still further embodiment of the dental implant.

FIG. 15 is a side view of FIG. 14.

FIG. 16 is a cross-sectional view of one embodiment of the post

FIG. 17 is a partially-sectional view showing a connection between the post and the blade.

FIG. 18 is a front view of a semi-submergible oral implant.

FIG. 19 is a cross section of an implant designed with legs that extend into the cortical plate and straddle the inferior alveolar nerve.

DESCRIPTION OF ILLUSTRATIVE EMBODIMENT

Although a specific embodiment of the invention will now be described with reference to the drawings, it should be understood that the embodiment shown is by way of example only and merely illustrative of but one of the many possible specific embodiments which can represent applications of the principles of the invention. Various changes and modifications, obvious to one skilled in the art to which the invention pertains, are deemed to be within the spirit, scope and contemplation of the invention as further defined in the appended claims.

Figure 1:
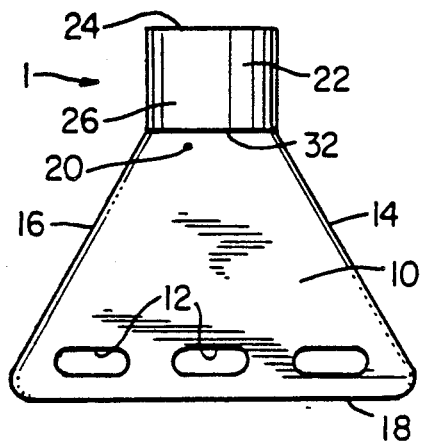
FIG. 1 is a view of a dental implant according to the present invention.

In FIG. 1 there is shown an enlarged embodiment of the invention. An oral implant 1 includes an implant portion in the form of a blade 10 and a post portion 22. In the embodiment of FIG. 1, the blade and the post are permanently attached to each other.

The blade 10 has holes or vents 12 which allow bone to grow completely through the blade so as to anchor the implant in place.

It is shown in FIG. 1 that the blade in the mesiodistal plane has a substantially triangular configuration with rounded off angle portions. However, other configurations of the plate are possible. The triangular blade 10 has sides 14 and 16 and a base 18. The width of the base 18 should be such as to allow tight engagement with an opening in a bone in which the implant is inserted.

A connection part 20 is located at the apex of the triangular plate i.e. opposite the base 18. A post portion 22 having a first end 24 and a second or base end 26 is attached to the connection part 20. The first end 24 receives at least a part of the artificial tooth structure. The base end 26 is adapted for a direct connection to the blade 10 without any intermediary elements. This connection is such that parts 32 and 34 in the bucco-lingual direction of the base 26 (FIG. 2) extend outwardly from the connection part of the blade. These extensions define a plurality of shoulders for receiving and supporting the artificial tooth structure. Also, by keeping the apex or connecting portion of the blade to the post as wide as possible there can be no weakness in the area which could otherwise cause bending or loss of bone.

Figure 2:
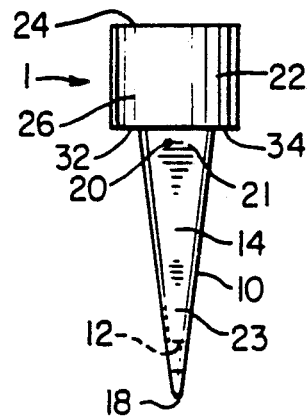
FIG. 2 is a side view of the dental implant of FIG. 1.

FIG. 2 shows that the plate 10 in the bucco-lingual plane has a wedge-shaped configuration with wide end 21 and narrow end 23. The connection part 20 of the plate is positioned at the wide end 21 of the wedge-shaped plate. Further, it can be seen that the narrow neck common to prior art devices has been eliminated. Instead, the post is even thicker than the blade over its entire length. This allows the post to resist the forces of mastication. In the view of FIG. 1 it can also be seen that the connection part 20 and the post 22 have great thickness in the mesial-distal direction so that a rigid structure in all directions is obtained.

Figure 3:
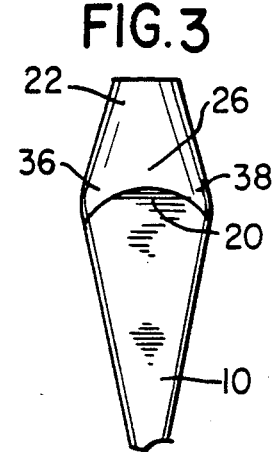
FIG. 3 is a side view of another embodiment of the dental implant.

In the embodiment of invention illustrated in FIG. 3, wings 36 and 38 of the base 26 of the post overlap a top portion of the connection part 20 in the bucco-lingual direction. This makes the transition between the post and the blade smoother, reducing even further the stresses common to the neck-type oral implants.

Figure 4:
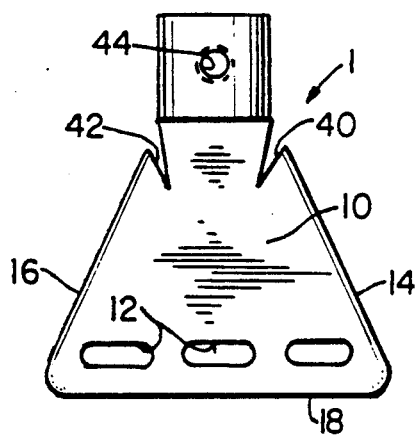
FIG. 4 is a view of still another embodiment of the dental implant.
Figure 5:
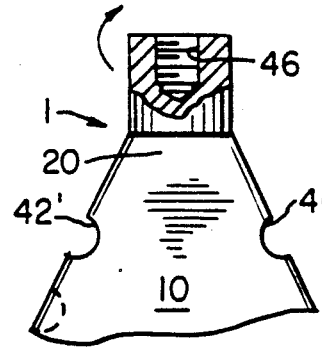
FIG. 5 is a partial view of a further embodiment of the dental implant.
Figure 6:
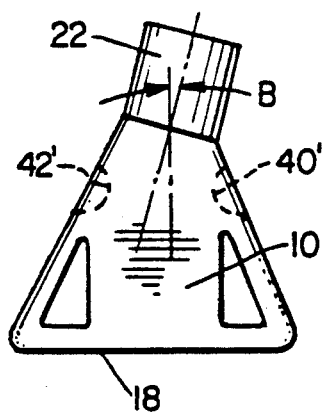
FIG. 6 is a front view of an additional embodiment of the invention.

To facilitate bending of the oral implant in the mesio-distal direction to align the artificial tooth with remaining natural teeth, a bending arrangement is provided within the blade of the invention. This bending arrangement is illustrated in FIG. 4 and includes at least two V-shaped slits or cavities 40, 42 extending from outer surfaces of the sides 14, 16 into the body of the blade. The cavities 40, 42 are positioned at an angle to and equidistantly spaced from the base 18 of the blade. However, alternative configurations of the cavities are possible. For example, FIG. 5 shows the cavities 40' and 42' having a semi-circular design. These cavities or the slits of FIG. 4 can be located at different heights on the implant. For example cavity 42' could be located at a lower point such as shown in dotted line on FIG. 5. When the post is bent in the mesial-distal direction, as shown by the arrow in FIG. 5, notch 42' tends to move upwardly and notch 40' tends to move downwardly so that the grooves tend to end up at about the same height as shown in dotted line in FIG. 6.

If, in order to align the post 22 with other teeth along the occlusal plane, an angle of inclination B (FIG. 6) of the post 22 to the blade 10 in the mesio-distal direction is needed, the implant may be bent as described. However, as an alternative, the oral implant may be manufactured by casting or otherwise with a post permanently positioned at the angle B to the blade in the mesio-distal direction. This angle may be, for example, 15°. In such a case the cavities 40′, 42′ shown in FIG. 6 need not be provided.

Figure 7:
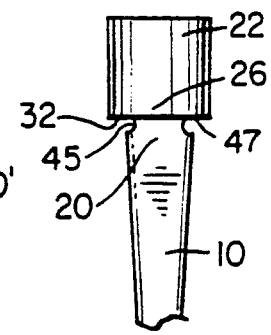
FIG. 7 is a side view of a still further embodiment of the invention.
Figure 8:
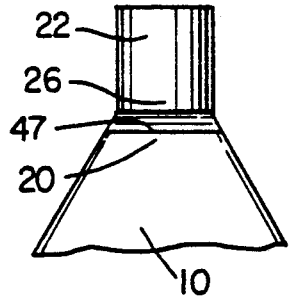
FIG. 8 is a front view of FIG. 7.

FIGS. 7 and 8 show an oral implant having a bending arrangement which facilitates bending in the bucco-lingual direction.

The bending arrangement of these figures includes two grooves 45 and 47 extending along both sides of the blade 10. The grooves are positioned at a place of connection between the second end 26 of the post and the connection part 20 of the blade.

Figure 9:
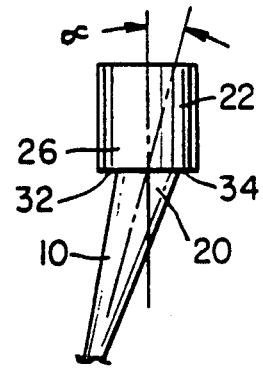
FIG. 9 is a side view of another embodiment of the invention.

An embodiment of FIG. 9 is manufactured with the post 22 positioned at an angle α to the blade 10 in the buccolingual direction. Similar to the embodiment of FIG. 6, the embodiment of FIG. 9 can be used when the required angle of inclination α is known in advance. Also, implants of this type can be cast with several standard offset angles for selection by the oral surgeon, e.g. 15°, 25°, etc.

The oral implant can have one post portion, as is shown in FIG. 1, or a plurality of the posts attached to the same blade. FIG. 10, illustrates an embodiment having two post portions 122 and 123 attached to the same blade 110. There are two connection parts 120 and 121 in the blade 110, each adapted to receive the individual post portion. A plurality of the posts can be used when a better support of an artificial dental structure by the oral implant is needed, i.e. to support dental bridges etc.

The posts can be circular, oval or rectangular with tapering or non-tapering outside walls.

The crown or the bridge can be attached to the oral implant by a screw or screws which pass through an opening in the crown or bridge into either horizontal threaded holes 44 in the post as shown in FIG. 4 or vertical threaded holes 46 as shown in FIG. 5. The vertical threaded hole and the screw inserted therein can be extended to penetrate through the post into the blade.

The oral implant of the invention can be provided with a post or posts removable from the blade. In that case (see Figs 11–13) a post 50 is provided with legs 52 and 54 projecting outwardly from the first end 56 of the post. In an assembled condition of the oral implant, the legs 52 and 54 straddle a recessed part 58 of the blade connection part. Initially it can be merely a frictional connection between the legs and the connection portion as shown in FIGS. 12 and 13. As shown in FIG. 13 the legs can have inward projections 62 and 64 that snap into grooves in the connection portion.

To provide a fixed connection between the post and the blade, a screw 60 (FIGS. 4 and 12) can be used. This screw passes through threaded openings in the legs 52 and 54 of the post and a threaded opening in the recessed part 58 of the connection portion.

FIG. 13 further shows that legs 52 and 54 are made wider than the connection part of the blade, thus providing buccolingual shoulders 66, 67 for support of the artificial tooth structure.

The embodiment of FIGS. 11, 12 and 13 may be made similar to the embodiment of FIG. 3, in that the lower parts of the legs (not shown in the drawings) can be extended to overlap the top portion of the connection part in the bucco-lingual direction.

FIGS. 14 and 15 illustrates an alternative to the design of FIG. 13 in which each leg of the post may fit within recesses in the connection part of the blade, so that the substantially flat outside surfaces of the legs fit flush with the buccal and lingual surfaces of the blade.

The post shown in FIGS. 14 and 15 does not have legs for engagement with the connection part of the blade. Instead, a cavity 70 is arranged in the central area of the second end of the post. The cavity 70 extends from an outer surface of the base of the post and is adapted to closely receive the connection part of the blade. A vertical or horizontal screw can be used to fixedly attach the post to the blade.

The oral implant of the invention can be installed by first making an incision in the fibromucosal tissue down to the underlying bone. The tissue is reflected and a groove is drilled in the bone using a burr. This groove is made about the width of the base of the blade. The blade can then be snugly fit therein in such a manner that at least a portion of the connection part of the blade extends beyond the plane of the bone. In some instances, the connection part can be positioned just below the rim of the opening in the bone, allowing the second end of the overlapping post to rest on the bone. Once the blade is in place, the tissue is sutured over the blade. Several weeks or months are allowed to pass before the dental prosthesis is attached to the post. During this period, the bone starts to grow around the implant portion and through the holes provided in it until surrounding bone becomes integrated with the blade. This is necessary to anchor the implant in place before it is stressed by use.

If a unitary blade and post are used, the next step is to install the artificial tooth structure on the post. If a separable post is used, the post must be attached to the connection part, e.g. by screws, before the prosthesis is installed.

The use of screws and similar devices for attachment of a post to a blade requires additional space for drilling of threaded holes in these elements of the implant. Placement of such a threaded connection can be time consuming and not always reliable. The present invention offers a new way of connecting the blade and the post which allows the oral surgeon to avoid the above disadvantages of the threaded connections.

In FIGS. 16 and 17, there is shown a post 80 with an inside cavity 82 that extends from an outer surface 84 of the base end 86 into its body. The cavity is designed for close engagement with the connection part 88 of a blade 90. At least the connection part 88 of the blade is made from a material softer than the material of the post.

A plurality of tiny rigid bubbles or rigid three dimensional raisings extend outwardly and inwardly from a surface of the cavity 83. One or more rough areas are thus defined by the bubbles within the surface 83. These bubbles can be created during the process of casting the post or may be etched therein.

The post can be connected to the blade by positioning the cavity of the post over the end of the connection part 88. A mallet or similar tool may be used to force the cavity 83 of the post onto the connection part 88 of the blade. As a result, the rigid bubbles of the post are crushed as the cavity is penetrated deeply by the connection part of the blade. This results in a cold weld locking of the two pieces together.

The various parts of each of the embodiments may be made of titanium, vitalism or surgical stainless steel. In the case of the embodiment of FIGS. 16 and 17, the relative hardness of these materials should be considered in selecting the materials and typically the post and blade would be made of different materials.

A semi-submergible dental implant 100 is shown in FIG. 18. This implant includes an implant portion 110 and a post portion 130 which are manufactured as two separate pieces. A connection part 120 of the implant portion is positioned at a place of connection between the implant portion and the post portion. The connection part 120 has a receiving element 122 for receiving at least a part of the post. The receiving element 122 extends outwardly from the implant portion in the direction of the occlusal plane for a short distance, e.g. 2-3 mm.

The post portion 130 has a first end 132 and a second or base end 134. The first end receives at least a part of the artificial tooth structure. The base end 134 is adapted for a direct engagement with the receiving element of the implant portion. The receiving element 122 has the lateral dimension as wide as the lateral dimension of the base end 134 of the post.

A fastening member 136 protrudes outwardly from the base end 134. The receiving element 122 has an opening 124 for receiving the fastening member 136. In the embodiment of FIG. 18 the fastening member 136 and the opening 124 have threads for mutual engagement.

The opening 124 is also adapted to receive a cap or plug 150. The plug is designed to be threaded into the opening for closing thereof. The plug and the implant can be made from the same material, i.e. titanium, vitalium or surgical stainless steel. As an alternative the plug can also be made of Teflon or another suitable plastic.

The implant of FIG. 18 is installed in a manner similar to the above discussed. However, a groove is drilled in the bone deep enough for the implant portion 110 to be submerged in the groove below its upper rim in such a manner that only the receiving element 122 of the connection part 120 protrudes outwardly from the groove in the direction of the occlusal plane.

However, element 122 is so short it does not extend above the gum tissue. Once the implant portion is in place, the plug 150 is threaded into the opening 124. The gum tissue is then sutured over the implant portion and the receiving element. As a result, only a very small part of the implant portion protrudes above the tissue. Thus the implant is protected from impact with the patient's tongue and other teeth.

During the waiting period the surrounding bone and tissue became integrated with the implant portion. However, the plug 150 prevents tissue growth in the opening 124.

Once the dentist is sure that the implant portion is firmly anchored in the bone, a new incision is made in the tissue and the plug is removed. In place of the cap, the post 130 is threaded into the opening 124.

When a patient's alveolar ridge bone 160 is wide, a groove can be made across the ridge bucco-lingually or labioplatally so as to span the soft medulary bone and include the tougher cortical bone near the surface of the ridge. In such a case the blade can be made with a cross section like that in FIG. 19. The blade of FIG. 19 has buccal and lingual legs 140, 142 connected by a transverse connection part 144 upon which post 146 is located. As shown, the outer edges of the legs are received in the cortical plate 150 but circumvent the inferior alveolar nerves 152 by straddling them. In this manner the implant can take advantage of the maximum available bone by extending into the area near or in the cortical bone, while avoiding the nerves.

The shape of the side of the implant of FIG. 19 may be like any of the other designs in this application or in common use. Also the cross-sectional shape may be modified in any convenient manner to conform to existing bone and nerve conditions. For example the legs may be parallel and vertical, instead of slanted toward each other as in FIG. 19. Also, the legs may slant away from each other and the portions surrounding the nerve may form a smooth curve. In determining which shapes to use or fashion, CAT scans and tomograms may be used to locate the nerve and to define the bone structures.

As with the other implants discussed, the implant of FIG. 19 may be made submergible by making the post detachable from the blade.

What is claimed is:

1. A submergible oral implant for supporting an artificial tooth structure, comprising:
    an implant portion having an upper surface, a bottom surface, side surfaces extending between the upper and bottom surfaces, and a connection part at an area of the upper surface, the connection part having sides and generally orthogonal ends, the distance between the sides of the connection part being as wide as the lateral dimension of the rest of the implant portion, the implant portion being adapted to be fitted with an opening in a bone in the vicinity of the occlusal plane of a patient in such a manner that said connection part remains just below the rim of the opening in the bone, and
    at least one post portion having first and second ends, the first end being adapted to receive at least a part of said artificial tooth structure and the second end being adapted for a direct connection to the connection part of the implant portion, the post portion having lateral dimensions such that a part of the second end extends outwardly at least to the sides of the connection part and defines shoulders for supporting the artificial tooth structure, the post portion having longitudinal dimensions such that another part of the second end extends outwardly at least to the ends of said connection part, the side surfaces of the implant portion in the mesio-distal plane being connected to the upper surface along a connection edge that slopes toward the bottom surface in the direction away from the connection part, whereby, upon insertion of the implant in the opening in the bone, the bone may grow over the implant portion to the connection part and no narrow neck portion is provided between the implant portion and the post portion.

2. An oral implant according to claim 1, wherein said implant portion has a substantially triangular configuration, said triangular configuration formed by sides of said implant portion extending obliquely from one another at the apex of the triangle, said connection part of the implant portion being positioned at the apex of the triangle and said shoulders of the second end of the post portion extend outwardly from sides of the triangle.

3. An oral implant according to claim 1, wherein said shoulders of the second end overlap surfaces of the connection part of the implant portion extending in the bucco-lingual direction.

4. An oral implant according to claim 1, wherein said shoulders extend in the bucco-lingual direction.

5. An oral implant according to claim 1, wherein a cross-section of the implant portion in the bucco-lingual direction has a wedge-shaped configuration with wide and narrow ends, the wide end being connected to the second end of the post portion.

6. An oral implant according to claim 1, wherein said implant portion further comprises bending means to enable the oral implant to bend in the mesio-distal direction, the bending means being located within the implant portion and spaced from the connection part.

7. An oral implant according to claim 6, wherein the bending means comprises at least one cavity extending in to a side of the implant portion on each side of the connection part, the cavities being positioned equidistantly from a base of the implant portion.

8. An oral implant according to claim 6, wherein the bending means comprises at least one cavity extending in to a side of the implant portion on each side of the connection part, the cavities being positioned at different distances from a base of the implant portion.

9. An oral implant according to claim 1, wherein said first end of the post portion has receiving means for receiving a fastener for fastening the artificial tooth structure to the post portion.

10. An oral implant according to claim 9, wherein said receiving means is an opening having an internal thread and adapted to receive a threaded shaft extending from said artificial tooth structure.

11. An oral implant according to claim 10, wherein said receiving means opening has a longitudinal axis generally parallel to the occlusal plane when the implant is installed.

12. An oral implant according to claim 10, wherein said receiving means opening has a longitudinal axis generally perpendicular to the occlusal plane when the implant is installed.

13. An oral implant according to claim 1, wherein a plurality of post portions are attached to the implant portion.

14. An oral implant according to claim 1, wherein the implant portion and the post portion are made from the same material, and the material is one of the group of titanium, vitalism or surgical stainless steel.

15. An oral implant according to claim 14, wherein the post portion is detachably connected to the implant portion and the second end of the post portion is adapted to straddle the connection part of the implant portion when connected thereto.

16. An oral implant according to claim 15, wherein the second end of the post portion has a pair of spaced-apart legs and the connection part of the implant portion has a pair of recesses, and wherein in the assembled condition of the oral implant, the legs fit within the recesses of the implant portion.

17. An oral implant according to claim 16, wherein at least one fastening means is provided for fastening the post portion to the implant portion.

18. An oral implant according to claim 17, wherein the fastening means comprises a screw which engages in a threaded opening through the legs of the second end and the connection part.

19. An oral implant according to claim 15, wherein a plurality of post portions are detachably attached to the implant portion.

20. An oral implant according to claim 1 wherein said connection part is a transverse part and the implant portion further comprises at least two leg parts extending from the traverse connection part in a direction opposite the post portion, the leg parts being spaced apart from each other a sufficient distance to avoid a patient's inferior alveolar nerve and to contact the cortical bone of the sides of the patient's alveolar ridge.

21. An oral implant according to claim 1, wherein the post portion is positioned at an angle in the mesio-distal direction to the implant portion.

22. An oral implant according to according to claim 1, wherein the post portion is positioned at an angle in the bucco-lingual direction to the implant portion.

23. A oral implant for supporting an artificial tooth structure, comprising:
an implant portion having a connection part, the implant portion being adapted to be fitted with an opening in a bone structure in the vicinity of the occlusal plane of a patient,
at least one post portion having a body, first and second ends, the first end being adapted to receive at least a part of the artificial tooth structure and the second end being adapted for a direct connection to the connection part of the implant portion, the post portion having a cavity for close reception of at least a part of the connection part and extending from an outer surface of the second end into the body of the post portion; and
means for forming a wedging cold weld locking of the implant portion and the post portion together upon assembly of the implant portion and the post portion, the forming means comprising a plurality of rigid three-dimensional raisings extending outwardly from an inside surface of the cavity, the raisings being crushed upon assembly of the implant portion and the post portion when the connection part extends into the cavity.

24. An oral implant for supporting an artificial tooth structure according to claim 23, wherein the post portion has the three dimensional raisings made of a material having a relative hardness substantially lower than the hardness of a material of the implant portion.

25. An oral implant for supporting an artificial tooth structure according to claim 23, wherein the three dimensional raisings are created during a process of casting the post portion.

26. An oral implant for supporting an artificial tooth structure according to claim 23, wherein the three dimensional raisings are etched on the inside surface of the cavity.

27. A semi-submergible oral implant for supporting an artificial tooth structure comprising:
an implant portion having an upper surface, a bottom surface, side surfaces extending between the upper and bottom surfaces, and a connection part extending outwardly from the rest of the implant portion in an area of the upper surface, the connection part being of limited extent such that when the implant portion is installed in a bone of a patient, the connection part may be covered by the patient's gum tissue, the connection part having a lateral dimension in the mesial-distal direction and a longitudinal dimension in the bucco-lingual direction that are at least as great as those of the adjacent portions of the implant portion,
at least one post portion having first and second ends, the first end being adapted to receive at least a part of the artificial tooth structure and the second end being adapted for a direct connection to the connection part, the implant portion being adapted to be fitted in an opening in the bone in the vicinity of the occlusal plane of the patient in such a manner that the implant portion is submerged below a rim of the opening and at least a portion of the connection part extends outwardly beyond the rim in the direction of the occlusal plane, the second end of said post portion having a lateral, i.e. mesial-distal, dimension as wide as the lateral dimension of the connection part and extending outwardly at least as far as the implant portion to define shoulders for supporting the artificial tooth structure, the side surfaces of the implant portion in the mesio-distal plane, being connected to the upper surface along a connection edge that slopes toward the bottom surface in the direction away from the connection part and begin at the junction of the connection part and the implant portion, whereby, upon insertion of the implant in the opening of the bone, the bone may grow over the implant portion to the connection part and no narrow portion is provided between the implant portion and the post portion.

28. A semi-submergible oral implant according to claim 27, wherein said post portion is detachably connected to the connection part, said post portion has a fastening member extending outwardly from said second end and said connection part has an opening for receiving a fastening element.

29. A semi-submergible oral implant according to claim 28, wherein said fastening member and said opening in the connecting part have threads for mutual engagement.

* * * * *